United States Patent
Lender et al.

(10) Patent No.: US 6,531,027 B1
(45) Date of Patent: Mar. 11, 2003

(54) ADHESIVE PRINTING PROCESS FOR DISPOSABLE ABSORBENT ARTICLES

(75) Inventors: Horst Andreas Lender, Rockingen (DE); Julian Ashton Plumley, Warsaw (PL)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/762,089

(22) PCT Filed: May 3, 1999

(86) PCT No.: PCT/US99/17555

§ 371 (c)(1),
(2), (4) Date: Jun. 28, 2001

(87) PCT Pub. No.: WO00/07532

PCT Pub. Date: Feb. 17, 2000

(30) Foreign Application Priority Data

Aug. 3, 1998 (EP) ............................................ 98114512

(51) Int. Cl.⁷ ........................... A61F 13/15; B05C 1/08; B32B 31/12
(52) U.S. Cl. ...................... 156/291; 156/548; 156/549; 156/578; 118/211; 118/212; 118/667; 427/208.2; 427/208.4; 427/428
(58) Field of Search ................................. 156/291, 578, 156/547–549; 118/211, 212, 667; 427/208.2–208.4, 398.2, 428

(56) References Cited

U.S. PATENT DOCUMENTS 5,225,240 A * 7/1993 Reichelt et al. ............. 101/163

FOREIGN PATENT DOCUMENTS

| DE | 19516037 A1 | * 11/1996 | ............. B05D/1/28 |
| EP | 0745433-a1 | * 12/1996 | ............. B05C/1/16 |
| WO | WO 9529765 A1 | * 11/1995 | ............. B05C/5/02 |

* cited by examiner

Primary Examiner—Sam Chuan Yao
(74) Attorney, Agent, or Firm—Roddy M. Bullock; Ingrid N. Hickman

(57) ABSTRACT

The present invention relates to a process for making disposable absorbent articles comprising adhering two components materials to each other using an improved roll printing process to provide an adhesive to one of the two components, the adhesive has an application temperature which is greater than a print roll temperature.

10 Claims, 3 Drawing Sheets

ADHESIVE PRINTING PROCESS FOR DISPOSABLE ABSORBENT ARTICLES

FIELD OF THE INVENTION

The present invention relates to a process for making disposable absorbent articles such as sanitary napkins, panty liners, catamenials, incontinence inserts, and diapers for adults or babies. In particular the present invention relates to a process for the manufacture of disposable absorbent articles comprising two component materials which are adhered to each other, which utilises an improved roll printing process to provide the adhesive.

BACKGROUND OF THE INVENTION

Absorbent articles such as sanitary napkins, panty liners, catamenials, incontinence inserts and diapers for adults or babies are commonly provided with an adhesive on their garment-facing surface to attach them during their usage period to a garment of the user. In particular sanitary napkins and panty liners are commonly provided with a pressure sensitive, hotmelt, adhesive which attaches to the undergarment of the wearer and thereby improves fit and comfort of the product for the wearer, called panty fastening adhesive. These adhesives are typically covered with a release paper prior to use.

More generally absorbent articles are provided with adhesive areas in order to combine the components which ultimately make up part or the whole of the absorbent article. In particular, multi-layer structures forming the topsheet, core or backsheet are often combined by adhesives called construction adhesives. The combining of the topsheet, the core and the backsheet to each other also can be accomplished by adhesives.

Typically these products are made by high speed machinery. The machinery includes equipment which adds the adhesive in a very fast and efficient manner, ensuring consistency of the absorbent products over large quantities thereof.

A common way of providing an adhesive is by application by slot-coating or spraying of the adhesive onto a continuously conveyed thread of material. The surface of this material, coated with adhesive, is then joined to another material forming all or part of the disposable absorbent article. This adhesive application method allows adhesive application with contact between the apparatus and the material to be coated, in particular for thermoplastic films or nonwoven materials often used in disposable absorbent articles which are very heat sensitive and can be incompatible with adhesives which require high melting temperatures.

An alternative method of adhesive application to material used in absorbent articles is a screen printing method. In the screen printing method, an adhesive is applied to the inside of a rotating roll having apertures. This roll, also called a screen, is contacted with the continuous conveyed thread of material such that adhesive is transferred through the holes of the material. In this case the screen is indirectly heated using infra-red radiation whereby the screen and to some extent the adhesive is heated.

Another alternative application method for adhesive is to render one of the materials used in the production of absorbent articles adhesive. This can be carried out in a separate step independent and long before use of the material in the article. For example adhesive tape or film, as used on baby diapers, have one adhesive surface and one non-adhesive surface. The adhesive surface is not firmly attached (or at least releasably attached) to the non-adhesive surface by winding the tape or film up into a roll. Upon use of the material the roll is then unwound to present the adhesive surface to the material to which it is intended to attach the tape or film.

For example U.S. Pat. No. 5,064,492 provides in this manner an impermeable film onto which a particular adhesive, which is said to be non-blocking below about 43° C. (110° F.), is printed. The adhesive is provided to the film by a patterned printing roll and a cooled counter roll or a series of such printing units if patterns in the adhesive are desired. The winding of the adhesive coated film is conducted below the blocking temperature.

This method of providing pre-coated film adds multiple complexities to logistics, storage and final manufacturing of disposable articles. Even accidental heating of any portion of the pre-coated roll would render it useless (self adhesion). Also all the benefits of the positioning accuracy of adhesive printing are lost in the alignment difficulties associated with film unwinding. Furthermore, the adhesive has to be heated on the film to return it to a state of adhesivity such that added energy consumption is paired with a probability of melting through the underlying film material. Also this heating of the adhesive causes degradation due to the added heating/cooling cycle.

One common drawback of all the above mentioned adhesive application processes is their inflexibility, inaccuracy relative to the shape of the adhesive to be applied and that they essentially can only provide the adhesive continuously. Alternatively, on/off systems for coating or spraying not only have the drawback of delay in their systems response but also generally the problems associated with accelerating and decelerating mass streams. For hollow drum screen printing it is possible to create a pattern in the screen which would allow to create adhesive patterns. However, this is limited in that the screen has to provide a fairly even distribution of adhesive application sites (holes) in order to exclude temperature variations resulting in unstable application processes. Also adhesive screen printing cannot provide an even, full surface adhesive coverage due to the maximum apertured dimensions and total open area of such a screen in respect to its stability.

Yet another alternative manner that can be utilised to apply adhesive to a surface requires the utilisation of printing rolls. Such rolls are described in for example EP 745 433 and U.S. Pat. No. 5,417,789. The latter discloses a continuous process for the manufacture of absorbent pads which requires the application of an adhesive to a barrier layer's outer surface utilising a rotary roll print process. Similarly, U.S. Pat. No. 3,327,708 discloses a laminated non woven web wherein a lightweight cellulose wadding web is bound to a web of synthetic fibres by printing adhesive in a regular open pattern onto the wadding.

However, whilst the utilisation of roll printing in principle also allows for the application of adhesives in patterns on surfaces, the process still has a number of problems associated with it. Typically, the print roll is continuously supplied with adhesive from an adhesive dip bath into which the roll is partially submerged and in which it is rotated. Naturally, the adhesive needs to be supplied in a large excess to allow the print roll to rotate through the adhesive bath and become coated with the adhesive. This of course requires a large amount of energy to be expended particularly in order to maintain the bath and adhesive at the required temperature. Moreover, the rotation of the roll within the bath causes the formation of air bubbles within the adhesive bath which results in the formation of foam. The foam is transferred to the roll and thereby results in the uneven distribution of the adhesive on the roll and consequently onto the substrate, even after scraping. Furthermore, the foam also collects on the scraper itself and is not readily removed therefrom whilst the process is operational. As a result, the process cannot be operated continuously, but, requires regular interruption in order to remove the excess adhesive collected at the scraper.

Yet another problem with the current roll printing process is that the amount and distribution of adhesive which is deposited from the print roll onto the substrate is extremely difficult to control. The amount of adhesive deposited is dependent upon, amongst others, the cohesive properties of the adhesive itself and the temperature at which the adhesive is supplied. In particular, cohesive adhesives tend to exhibit a phenomenon known as stringing during the transfer of the adhesive from the roll to the substrate surface. This results in an irregular application of the adhesive to the surface, in addition to contamination of the adhesive pattern itself. This problem is further exacerbated when the printing process is operating at low temperatures. However, whilst desirable in terms of improved uniform distribution of the adhesive onto the roll and hence the substrate, increasing the operating temperatures of such printing processes is not usually feasible, because as previously mentioned the components of the disposable absorbent articles onto which the adhesives are applied, are typically temperature sensitive and hence the process needs to be operated below a certain maximum temperature.

Hence, there still exists a need to provide an improved adhesive application method to substrate components of disposable absorbent articles which addresses the aforementioned problems, whilst providing the adhesive in a continuous process, which is also accurate and efficient. Moreover there is also a need to provide a application method which preferably allows the provision of adhesive area shape designs so far not possible at the production speeds typical for disposable absorbent articles.

It has now been surprisingly found that these problems can be addressed by the direct application of the adhesive onto the roll printing by utilisation of techniques such as slot coating, whereby the temperature of the adhesive at application is greater than the temperature of the printing roll.

SUMMARY OF THE INVENTION

The present invention relates to a process for providing a disposable absorbent article comprising a first component and a second component material which are joined by adhesive. The first component comprises a first surface and the second component comprises a second surface. The process comprises the steps of;

a) providing said first component in a machine direction,
b) providing a printing roll with an adhesive
c) contacting said first surface of said first component with said printing roll and transferring at least a portion of said adhesive from said roll to said first surface
d) providing said second component and contacting said first surface of said first component with said second surface of said second component, characterised in that;
said adhesive has an application temperature $T_a$ and said roll has a roll temperature $T_r$, wherein $T_a$ is greater than $T_r$.

The roll printing step of the process according to the present invention is preferably conducted by a rotating printing roll for transporting the adhesive. The printing roll rotates such that during its 360 path it has a receiving rotation path and a delivery rotation path. The printing roll receives the adhesive in a receiving portion of its rotation path and delivers adhesive to the first surface in the delivering portion of the rotation path of the printing roll. Accordingly, the adhesive is applied to the printing roll at a temperature $T_a$ which is greater than the temperature of the printing roll itself $T_r$. The adhesive is typically a hot melt adhesive which is solid or in a semi-solid plastic state at temperatures at or below the usage temperature of the disposable absorbent product in which the adhesive is utilised. The adhesive is applied in a liquefied state, typically achieved by melting.

Preferably, the adhesive is applied at a temperature $T_a$ which is at least 5° C. greater than the temperature of the print roll $T_r$. More preferably the adhesive has a minimum application temperature $T_a$ of 110° C. or more.

The adhesive area can provide a releasable attachment means such as is typical between a release paper and a panty fastening adhesive. However, the current process is not limited to such adhesive application but can also provides a permanent connection between the first and the second components.

DETAILED DESCRIPTION OF THE INVENTION

Figure 1:
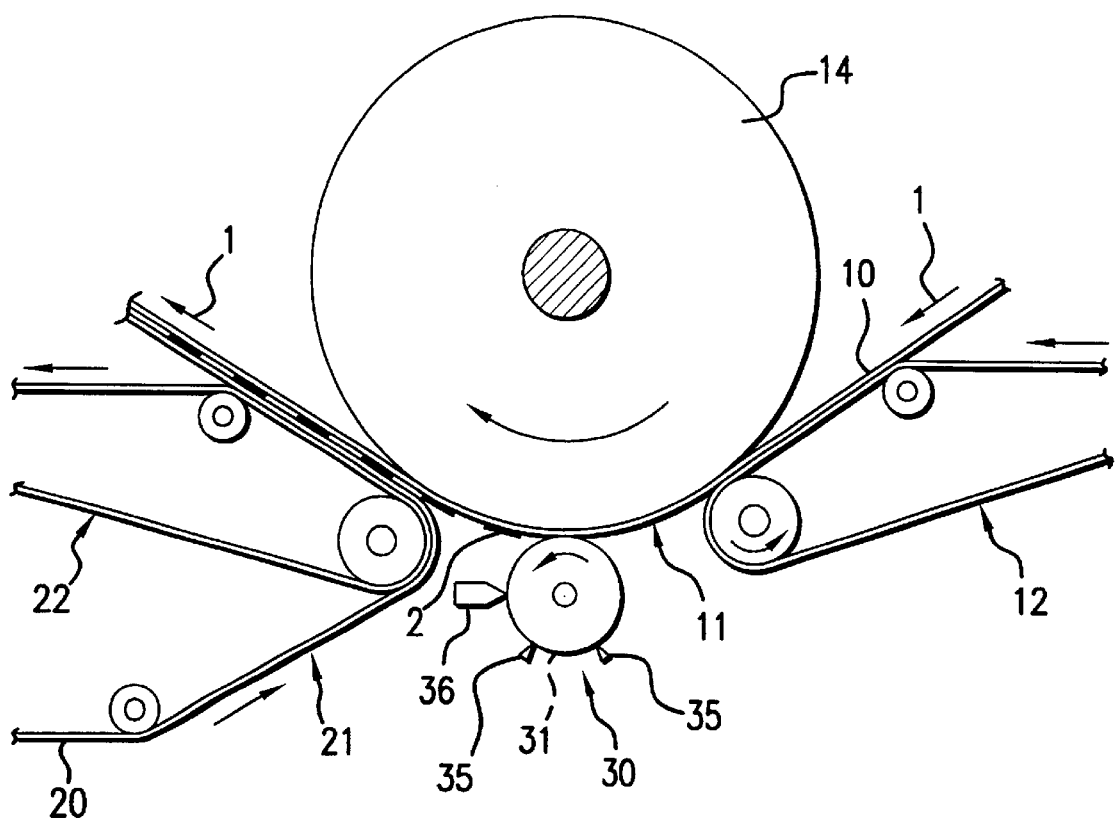
FIG. 1 shows a schematic view of an embodiment of the process steps of the present invention.

The present invention relates to a process for providing a disposable absorbent article comprising a first component and a second component material which are joined to one another by adhesive. The components may be any of the materials typically utilised in the context of disposable absorbent articles.

The absorbent article of the present invention has a wearer facing surface, typically provided by a liquid permeable substrate of fibrous or film like structure often termed topsheet; a garment facing surface, preferably provided by a liquid impermeable substrate, referred to as a backsheet which is preferably also moisture vapour permeable and hence breathable and, an absorbent structure placed between the wearer facing surface and the garment facing surface, typically termed the absorbent core.

The absorbent article can also comprise any of the components or features usual in the art, in particular side wrapping elements, side flap components, or wings as well as any sort of extensibility or elastication feature. In the production of absorbent articles several adhesive connections are typically formed all of which, some of which or at least one of which utilises the process according to the present invention. For example, a typical sanitary napkin or panty liner comprises an adhesive area on the garment facing surface of the backsheet providing the panty-fastening adhesive which is covered by a release paper, wrapper or the like prior to use of the article.

The absorbent article for absorbing liquid is described below by reference to a sanitary napkin or panty liner.

However products such as adult or baby diapers, or incontinence products comprising adhesives can similarly benefit from the process of the present invention.

The adhesives suitable for use in the present invention can be any adhesive known in the art so as to provide permanent or releasable attachment between two adjacent surfaces, such as hot melt adhesives, typically utilised for the panty fastening adhesives. Typically, hot melt adhesives, which comprise a thermoplastic base material, in combination with a tackifying resin, and mineral oils or waxes or a mixture of various such materials are preferred. Typical hot melt adhesives have a minimum melting temperature of about 80° C., often even about 100° C. The requirement for these hot melt adhesives is of course that they maintain their adhesive performance until disposal of the disposable absorbent article, i.e. during manufacturing, storage, transport and use of the disposable absorbent article. Typically, the highest temperature after manufacture is the usage temperature at about 40° C. when the disposable absorbent article is used on the body of a human. However, higher temperatures can occur for example when articles are left in a vehicle in the sun, where temperatures of 60° C. and higher have been reported.

When applying the adhesive by roll printing according to the present invention, it is necessary that the internal forces of the adhesive are greater than the adhesive forces to the roll and/or to the substrate to which the adhesive is printed so that the adhesive can be removed from the roll, whilst maintaining the adhesives' structural integrity. If this force relation is not met, sections of the substrate will disassociate themselves from the substrate and become attached to the printing roll. In order to ensure that this does not occur, it is necessary to maintain the operational temperature of the process within certain limits, since the cohesive strength of hot melt adhesives is highly dependent on the temperature of the adhesive. It is understood by those skilled in the art that simple trials will allow to immediately confirm whether for a given adhesive, the adhesive roll printing to a certain substrate can be performed and at which temperature.

According to the present invention the topsheet, backsheet and absorbent core components are joined together to provide the absorbent article. Typically, at least two, preferably all of the components of the article are joined to form the article.

Each of said components of the absorbent article comprise at least one layer which has a wearer facing surface and a garment facing surface. Typically, garment facing surfaces form a common interface with the wearer facing surface of an adjacent component or layer. The components or layers are joined together across this common interface. In this manner, the topsheet is joined to the absorbent core, and the core is joined to the backsheet. Furthermore, each of said topsheet, backsheet and core components may comprise more than one layer and these layers may also be similarly joined. In addition, the topsheet may be directly or indirectly joined to the backsheet at the periphery of the absorbent article and in the wings if present. Furthermore, particularly for sanitary napkin, panty liner and incontinence product applications, the garment facing surface of the backsheet provides the surface to which the absorbent article is joined to the garment of the user of the product to provide the panty fastening adhesive. Similarly if the product is a winged product, the wings are also provided with adhesive in order to secure the wings to the garment facing surface of the undergarment. These surfaces are typically provided with protective covers which are removed prior to use.

Hence, according to the present invention at least one of the wearer or garment facing surfaces of the topsheet, core or backsheet components comprises an adhesive applied according to the process of the present invention. Preferably, at least the garment facing surface of the backsheet is applied with an adhesive area according to the present invention. More preferably at least the garment facing surface of the backsheet and at least one other surface are joined to another by application of the adhesive area of the present invention and most preferably all of the common interfaces of the components of the article are joined together by the application of adhesive in the manner of the present invention.

The present invention will now be described with reference to the application of a panty fastening adhesive to the garment facing surface of the backsheet. However, as discussed herein above the invention is equally applicable for the adhesion of the common interface between any of the other surfaces of the components of the absorbent article.

According to a preferred embodiment of the present invention wherein the absorbent article finds utility as a sanitary napkin or panty liner, the adhesive is applied to the garment facing surface of the backsheet to provide the article with a panty fastening means which provides means to attach the article to the wearer facing surface of the undergarment. In addition, the panty fastening adhesive preferably provides a means for securing the article when soiled, to the fold and wrap package for convenient disposal. Typically, at least a portion of the garment facing surface of the backsheet is coated with pressure sensitive adhesive to form the panty fastening adhesive.

Panty-fastening-adhesives can comprise any adhesive used in the art for such purposes. These adhesives typically are pressure sensitive and remain tacky well below their application temperature. Suitable non-extensible adhesives are Savare LA203 manufactured by Savare I. C. Milan, Italy and Fuller H-2238ZP manufactured by the H.B. Fuller Co. in Lueneburg, in Germany. Suitable adhesive fasteners are also described in U.S. Pat. No. 4 917 697.

Prior to use of the absorbent article the panty fastening adhesive is typically protected from contamination and from adhering to another surface where this is not desired, by a protective cover means such as a silicone coated release paper, a plastic film or any other easily removable cover. The protective cover means can be provided as a single piece or in a multitude of pieces e.g. to cover the individual adhesive areas. It also can perform other functions such as provide individualised packaging for the article or provide a disposal function. Any commercially available release paper or film may be used. Suitable examples include BL 30MG-A SILOX EI/O, BL 30 MG-A SILOX 4 P/O available from Akrosil Corporation, and M&W films available from Gronau in Germany, under the code X-5432.

If protective side flaps or wings are present then they may also be provided with optional fasteners thereon for additional security. The fasteners assist the protective side flaps to remain in position after they have been wrapped around the edges of the crotch surface of the undergarment by adhering to the garment facing surface of the undergarment. Hence, the adhesive area applied in the wings is independent from the adhesive area applied as the so called panty fastening adhesive on the backsheet. The fasteners of the side flaps may also be applied with adhesive areas according to the present invention and are typically also covered with a protective cover means.

Process Steps of the Present Invention

In the following the process according to the present invention will be described with reference to the drawings.

Figure 2:
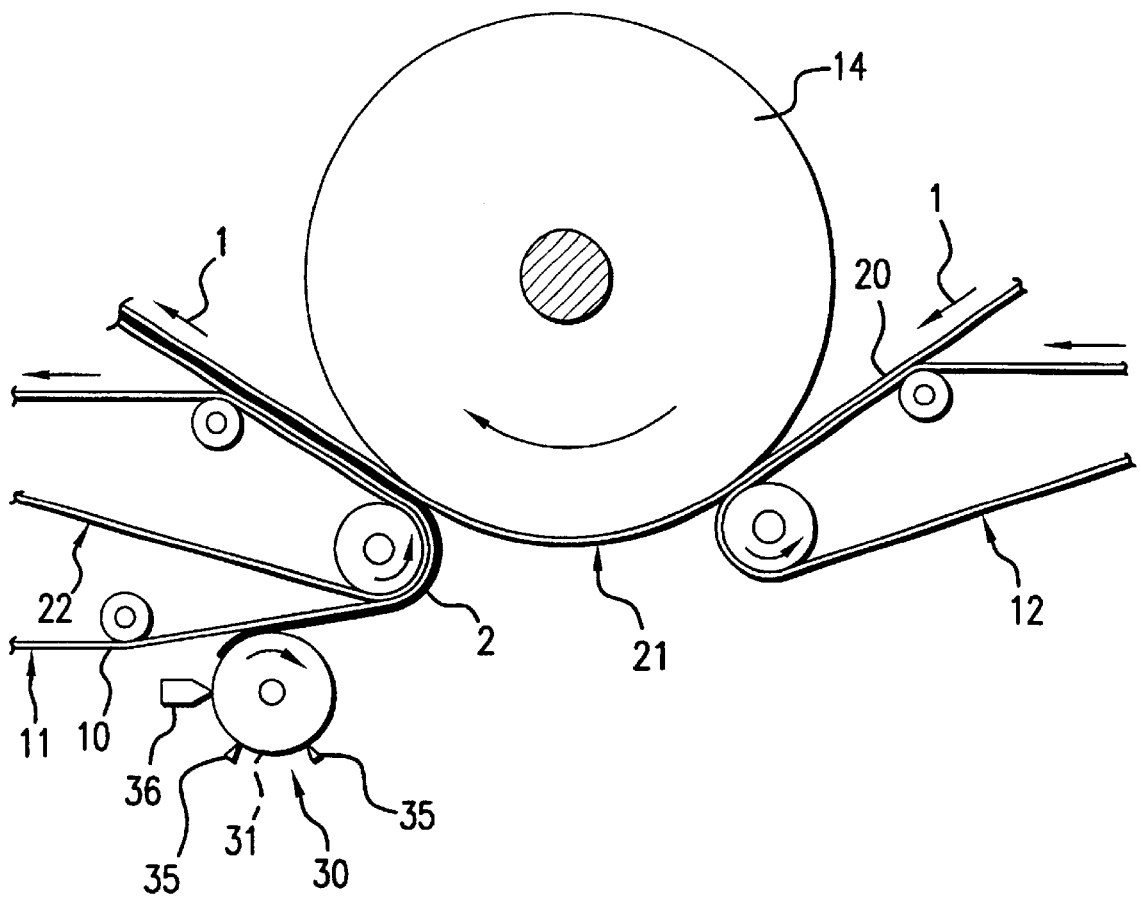
FIG. 2 shows an alternative embodiment to FIG. 1 with the adhesive printing located differently.

In FIG. 1, a process according to the present invention is shown, wherein a first component (10) is provided and conveyed in the machine direction, designated 1, following the transport path of the first component (10). A second component (20) is also provided and conveyed. FIG. 1 and FIG. 2 further show a schematic roll printing unit (30) where adhesive (2) is provided to the first surface (11) of the first material (10). In FIG. 1 and the detailed cross-sectional FIG. 3, the adhesive (2) is provided to the first surface (11) in an intermittent fashion. FIG. 2 shows a continuous delivery of adhesive (2) to the first surface (11) of the first component (10). In FIG. 2 the roll printing unit (30) is also provided at a different location than in FIG. 1 and is below but not directly under the first component (10) in a gravitation sense.

Figure 3:
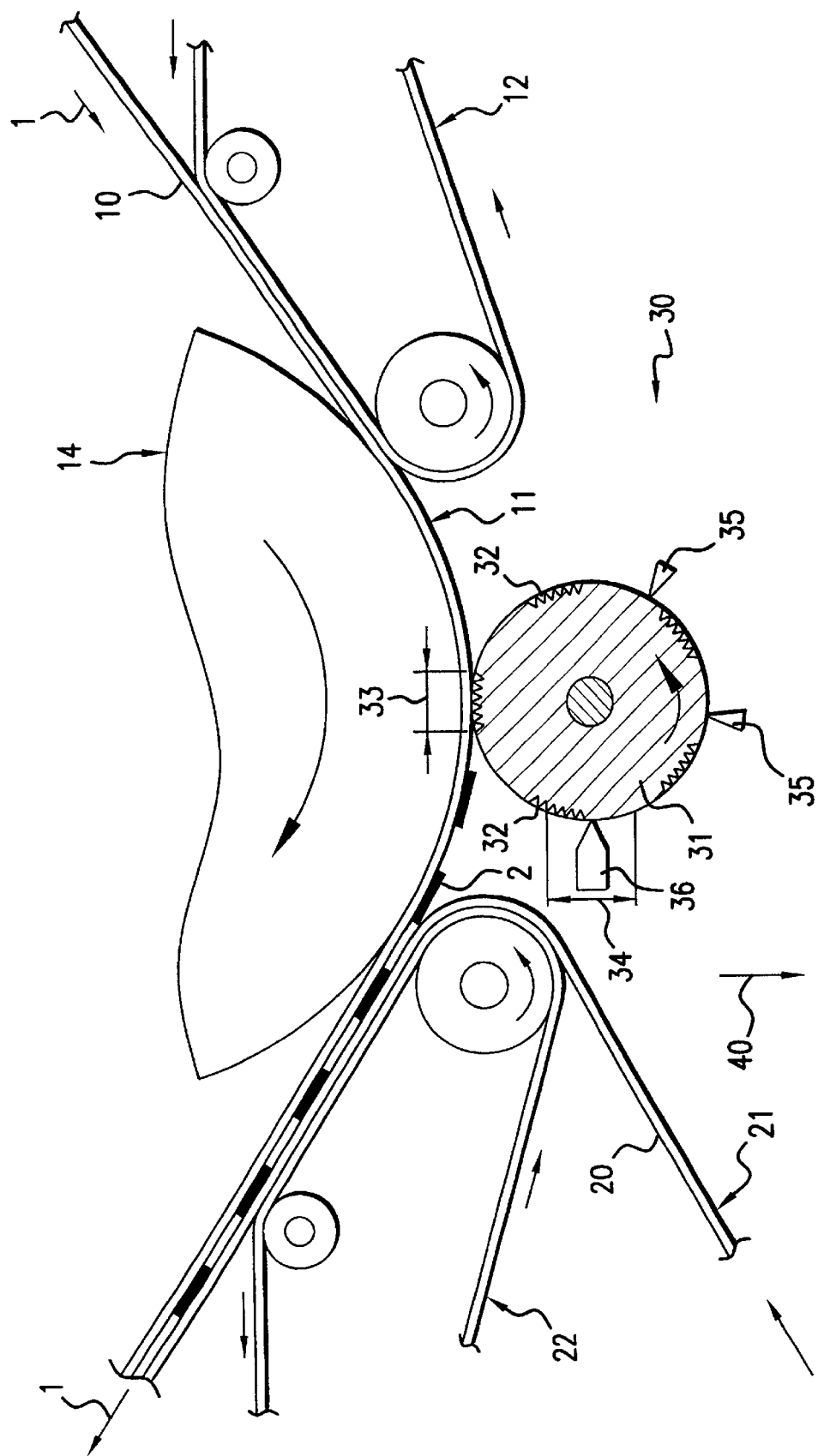
FIG. 3 shows a cross-sectional schematic view of the printing equipment used in the adhesive printing step according to the present invention.

Turning to FIG. 3 it can be seen that the first component (10) is conveyed in a machine direction (1) generally from the right hand side of the drawing guided by a material guiding system (12). The first component (10) may be a continuous web as shown in the diagram or it may be discrete articles. In the latter case the material guiding system is then selected appropriately. From this guiding system the first component (10) is transferred to another material guiding system (14) conveying the material (10) towards the roll printing unit (30).

The roll printing unit (30) comprises a rotating printing roll (31). The circular cross-section of the surface of rotating printing roll (31) describes the rotating path of rotating printing roll (31). The roll (31) in the receiving portion of the rotating path (34) is directly applied with an adhesive. Any means known in the art to apply the adhesive onto the roll may be used such as slot coating, spraying and applicator rolls. Preferably, the adhesive is applied by slot coating (36). According to the present invention the adhesive can be advantageously applied to the printing roll at a temperature $T_a$, which is greater than the operating temperature of the print roll $T_r$. Typically the temperature difference of the adhesive at application roll $T_a$, is at least 5° C., preferably at least 10° C., more preferably at least 20° C. and is most preferably at least 30° C. greater than the temperature of the print roll $T_a$ Typically, the adhesive is thus applied at a temperature of at least 110° C., more preferably at least 125° C., most preferably at at least 145° C. The exact adhesive application temperature $T_a$ will naturally be, to at least some extent, dependent upon the nature of the adhesive itself and can be readily selected in order to ensure sufficient viscosity of the adhesive, depending on the application method utilised in order to provide a thin continuous film. The roll (31) can and preferably is operational at an elevated room temperature $T_r$, which is less than the temperature of the adhesive at application $T_a$. In order to heat the roll, the roll is typically provided with internal heating elements such as hot oil or electrical heating elements to maintain the surface of transport roll (31) at the desired constant temperature $T_r$. Typically the operating temperature of the roll is less than 130° C., more preferably less than 120° C., most preferably less than 110° C. In addition the print roll temperature is also preferably greater than 90° C., more preferably greater than 100° C. in order to ensure that the adhesive is sufficiently viscous to allow scraping. Typically, the temperature of the print roll $T_r$ is also selected considering the nature of the first component substrate to ensure their compatibility.

By providing the adhesive onto the roll at a temperature greater than that of the operational roll temperature it has been surprisingly found that the amount of adhesive which is transferred from the roll to the surface of the component substrate can also be controlled such that typically at least 75%, preferably at least 80%, and most preferably substantially all of the adhesive contained within the gravures of the roll is transferred to the substrate. Whilst not intending to be bound by theory it is believed that this is due in part to the partial filling of the gravures, which are typically filled with adhesive less than 85%, preferably less than 70% of adhesive. More importantly, it is believed that using this process the adhesive can be applied to the roll in a more controlled manner such that the amount of adhesive applied to the roll can be readily adjusted and controlled minimising waste. In addition the significant reduction in stringing of the adhesive and the absence of air bubbles or foaming of the adhesive often present with adhesive bath applications, also assists in the desired controlled manner of adhesive application. Consequently, the amount of adhesive that is applied to the roll and subsequently the substrate can be readily controlled. Moreover since the temperature of the roll is not required to be maintained at the same temperature as the adhesive application temperature and the absence of the requirement of a adhesive bath, the costs of the process are considerably reduced.

The transport roll (31) is coated with the molten adhesive in the receiving portion of rotating path (34). The roll surface continuously moves along the rotating path and all excess adhesive is removed from the rotating transport roll (31) by a scraper blade (35) or a series of scraper blades. The scraper blade (35) essentially rides on the surface of rotating transport roll (31). It can be kept at a constant nip by distance rings or other spacing mechanisms. It also can be provided with constant pressure onto the roll by spring loading scraper plate (35) or other means well known in the art of printing.

A material guiding system (14) provides the support for the first component (10) during printing such that a printing pressure above the breaking pressure of the first material can be used and to ensure good contact with the roll. If first component (10) can withstand the printing pressure without support then the guiding system (14) and or is stiff enough to ensure contact the support is not absolutely necessary but desirable for printing placement accuracy.

The component (20) is provided and introduced into the process according to the present invention by a guidance system (22) as shown in FIG. 3. The distance between the point of joining second component (20) with second surface (21) to first component (10) by interfacing the adhesive (2) between first surface (11) and second surface (21) needs to be carefully set in order to ensure that the adhesive is still in a state to provide the desired adhesive attachment between both materials. If the combined components do not already represent the final disposable absorbent article it is then further conveyed to additional process steps to ultimately provide a disposable absorbent article.

The pattern of the adhesive provided to the first surface of the first material can be defined by the printing surface of the rotating printing roll (31). For example in FIG. 3 engravings or gravures (32) can be provided in any desired pattern. The required printing roll surface, which is typically larger than the surface of the component to be contacted with the adhesive will be covered by the adhesive in the receiving part of the rotating path of the transport roll (31). At the scraper plate (35) adhesive clinging to the roll surface outside the engravings (32) is removed and recycled. Only the engravings thereby remain filled or partially filled with the adhesive. The adhesive is then transported to the delivering portion of the rotation path of the rotating printing roll.

The "pattern of engravings" as used herein refers to the macroscopic area which is provided as adhesive area onto the first surface. This pattern is formed of a multitude of engravings which are typically small enough to provide the whole area of adhesive with a layer of adhesive of about constant quantity per surface area. Other adhesive applications may require other patterns such as a peripheral edge pattern to join the backsheet to the topsheet around the periphery of an absorbent core. The number of alternatives is unlimited but suitable patterns for the application will typically be easily identified by those skilled in the art.

As will be obvious for those skilled in the art, the shape, depth, and density of individual engravings on the rotating transport roll surface in addition to the overall pattern of the engravings will be a critical parameter for the total amount of adhesive and basis weight supplied to first surface (11) of first material (10).

The dimensions and density of these engravings can thus vary depending on the desired result of the adhesive printing step of the present invention. In the following preferable ranges for the engravings are given.

Each individual engraving can have a depth of from 0.01 mm for very small amounts of adhesive to be provided to 0.8 mm for the transport of large quantities of adhesive. Preferably the engravings have a depth of form 0.06 mm to 0.09 mm. An engraving size of 0.05 mm up to 3.0 mm, preferably from 0.1 mm to 2.0 mm as the side length for rectangular engravings or as the diameter for circular engraving has been found useful. For engravings which are neither square nor circular similar dimensions as those for square or circular engravings will be easily definable for those skilled in the art. The dimensions are of course taken on the surface of the rotating transport roll. A distance between engravings of 0.5 times to 50 times their depth has been found useful to provide an approximately even adhesive quantity distribution across the total engraved pattern.

The number of engravings per area depends on the individual engraving size. With increasing number of engravings and reducing size of individual engraving a more even adhesive delivery across the whole adhesive area will be achieved. Preferably the number of engravings/cm is from 2 to 150, preferably from 5 to 50 and most preferably from 5 to 20. The resulting percentage surface area coverage of the adhesive on the surface of the substrate component is from 20% to 95%, preferably from 45% to 75%.

An example of an engraving which has been successfully used in the context of the present invention is the engraving with a depth of 0.067 mm, a size of 0.8 mm times 0.8 mm and 100 engravings per cm$^2$. These engravings were used to provide a panty fastening adhesive onto a polyethylene backsheet of a sanitary napkin according to the general description above. If the desired, the panty fastening adhesive area can follow the peripheral outline of the sanitary napkin in a so-called dog-bone-shape in the narrowest part of the pad at a distance of approximately 4 mm. Typically the actual amount of adhesive which is applied on a particular surface is also dependent on the type of absorbent article itself and the physical and chemical nature of the materials of the surfaces which are to be joined. Preferably, the adhesive is applied at a basis weight of from 1 g/m$^2$ to 60 g/m$^2$. For adhesive applications to join the components of the article such as the topsheet, core and backsheet the basis weight is typically from 2 g/m$^2$ to 50 g/m$^2$, more preferably from 3 g/m$^2$ to 30 g/m$^2$. For application as a panty fastening adhesive, the adhesive is typically applied at a basis weight of from 5 g/m$^2$ to 50 g/m$^2$, preferably from 15 g/m$^2$ to 35 g/m$^2$.

Whilst it is preferred that the components of the article are also joined to one another utilising the adhesive area application of the present invention, these surface may also be joined by other means, known in the art for affixing two adjacent layers of material, such that the layers are directly attached to one another or directly attached to one another via the joining means. Suitable joining means include fusion bonding, ultra sonic bonding, stitching, heat (e.g. crimping), embossing, and/or pressure bonds, or dynamic mechanical bonds.

In order to more fully assess the utility of the process of the present invention a description of a typical disposable absorbent article follows.

The Topsheet

The topsheet is compliant, soft feeling, and non-irritating to the wearer's skin. The topsheet also can have elastic characteristics allowing it to be stretched in one or two directions in portions of the topsheet or throughout its extension. Further, the topsheet is fluid pervious permitting fluids (e.g., menses and/or urine) to readily penetrate through its thickness. A suitable topsheet can be manufactured from a wide range of materials such as woven and non woven materials; polymeric materials such as apertured formed thermoplastic films, apertured plastic films, and hydroformed thermoplastic films; and thermoplastic scrims. Suitable woven and non woven materials can be comprised of natural fibers (e.g., wood or cotton fibers), synthetic fibers (e.g., polymeric fibers such as polyester, polypropylene, or polyethylene fibers) or from a combination of natural and synthetic fibers or bi-/multi-component fibers.

Preferred topsheets for use in the present invention are selected from high loft nonwoven topsheets and apertured formed film topsheets. Apertured formed films are especially preferred for the topsheets because they are pervious to body exudates and yet non absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135; U.S. Pat. No. 4,324,246; U.S. Pat. No. 4,342,314; U.S. Pat. No. 4,463,045; and U.S. Pat. No. 5,006,394. Particularly preferred micro apertured formed film topsheets are disclosed in U.S. Pat. No. 4,609,518 and U.S. Pat. No. 4,629,643. A preferred topsheet for the present invention comprises the formed film described in one or more of the above patents and marketed on sanitary napkins by The Procter & Gamble Company of Cincinnati, Ohio as "DRI-WEAVE".

Topsheets having not a homogeneous distribution of liquid passage ways but only a portion of the topsheet comprising liquid passage ways are also contemplated by the present invention. Typically such topsheets would have the liquid passage ways oriented such that they result in a centrally permeable and peripherally impermeable topsheet for liquids.

The body surface of the formed film topsheet can be hydrophilic so as to help liquid to transfer though the topsheet faster than if the body surface was not hydrophilic. In a preferred embodiment, surfactant is incorporated into the polymeric materials of the formed film topsheet such as is described in PCT publication WO 93/09741. Alternatively, the body surface of the topsheet can be made hydrophilic by treating it with a surfactant such as is described in U.S. Pat. No. 4,950,254.

Another alternative are so called hybrid topsheets which incorporate fibrous and film like structures particularly useful embodiments of such hybrid topsheets are disclosed in PCT publications WO 93/09744; WO 93/11725 or WO 93/11726.

The topsheet typically extends across the whole of the absorbent structure and outside the area coextensive with the absorbent structure. The topsheet can extend and form part or all of the preferred side flaps, side wrapping elements or wings.

When referring to the topsheet a multi layer structure or a mono layer structure is contemplated. The hybrid topsheet mentioned above is such a multi layer design but other multi layer topsheets such as primary and secondary topsheet designs are also considered.

Absorbent Core

According to the present invention the absorbent cores suitable for use in herein may be selected from any of the absorbent cores or core system known in the art. As used herein the term absorbent core refers to any material or multiple material layers whose primary function is to absorb, store and distribute fluid.

According to the present invention, the absorbent core can include the following components: (a) an optional primary fluid distribution layer preferably together with a secondary optional fluid distribution layer; (b) a fluid storage layer; (c) an optional fibrous ("dusting") layer underlying the storage layer; and (d) other optional components.

a Primary/Secondary Fluid Distribution Layer

One optional component of the absorbent core according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilized. The fluid distribution layers can be comprised of any material typical for such distribution layers.

b Fluid Storage Layer

Positioned in fluid communication with, and typically underlying the primary or secondary distribution layers, is a fluid storage layer. The fluid storage layer can comprise any usual absorbent material or combinations thereof. It preferably comprises absorbent gelling materials usually referred to as "hydrogel", "superabsorbent", "hydrocolloid" materials in combination with suitable carriers.

The absorbent gelling materials are capable of absorbing large quantities of aqueous body fluids, and are further capable of retaining such absorbed fluids under moderate pressures. The absorbent gelling materials can be dispersed homogeneously or non-homogeneously in a suitable carrier. The suitable carriers, provided they are absorbent as such, can also be used alone.

Suitable absorbent gelling materials for use herein will most often comprise a substantially water-insoluble, slightly cross-linked, partially neutralised, polymeric gelling material. This material forms a hydrogel upon contact with water Such polymer materials can be prepared from polymerizable, unsaturated, acid-containing monomers which are well known in the art.

Suitable carriers include materials which are conventionally utilised in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins and panty liners.

An embodiment of the absorbent structure made according to the present invention comprises a double layer tissue laminate formed by folding the tissue onto itself. These layers can be joined to each other for example by adhesive or by mechanical interlocking or by hydrogen bridge bands. Absorbent gelling material or other optional material can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the absorbent gelling material is dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing absorbent gelling materials partially or fully.

c Optional Fibrous ("Dusting") Layer

An optional component for inclusion in the absorbent core according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the Absorbent Structure

The absorbent core according to the present invention can include other optional components normally present in absorbent webs. For example, a reinforcing scrim can be positioned within the respective layers, or between the respective layers, of the absorbent core. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

Another component which can be included in the absorbent core according to the invention and preferably is provided close to or as part off the primary or secondary fluid distribution layer are odor control agents.

Backsheet

The backsheet primarily prevents the extrudes absorbed and contained in the absorbent structure from wetting articles that contact the absorbent product such as underpants, pants, pyjamas and undergarments. The backsheet is preferably impervious to liquids (e.g. menses and/or urine) and is preferably manufactured from a thin plastic film, although other flexible liquid impervious materials can also be used. As used herein, the term "flexible" refers to materials that are compliant and will readily conform to the general shape and contours of the human body. The backsheet also can have elastic characteristics allowing it to stretch in one or two directions.

The backsheet typically extends across the whole of the absorbent structure and can extend into and form part of or all of the preferred sideflaps, side wrapping elements or wings.

The backsheet can comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils).

Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matt finished to provide a more clothlike appearance.

Further, the backsheet can permit vapours to escape from the absorbent structure, i.e. be breathable, while still preventing extrudates from passing through the backsheet. Also breathable backsheets comprising several layers, e.g. film plus non-woven structures, can be used. Such backsheets thus comprise at least one gas permeable layer. Suitable gas permeable layers include 2 dimensional, planar micro and macro-porous films, macroscopically expanded films, formed apertured films and monolithic films. The apertures in said layer may be of any configuration, but are preferably spherical or oblong and may also be of varying dimensions. The apertures preferably are evenly distributed across the entire surface of the layer, however layers having only certain regions of the surface having apertures are also envisioned.

Suitable 2 dimensional planar layers of the backsheet may be made of any material known in the art, but are preferably manufactured from commonly available polymeric materials. Suitable materials are for example Gortex (TM) or Sympatex (TM) type materials well known in the art for their application in so-called breathable clothing. Other suitable materials include XMP-1001 of Minnesota Mining and Manufacturing Company, St. Paul, Minn., USA and Exxaire XBF-101W, supplied by the Exxon Chemical Company. As used herein the term 2 dimensional planar layer refers to layers having a depth of less than 1 mm, preferably less than 0.5 mm, wherein the apertures have an average uniform diameter along their length and which do not protrude out of the plane of the layer. The apertured materials for use as a backsheet in the present invention may be produced using any of the methods known in the art such as described in EPO 293 482 and the references therein. In addition the dimensions of the apertures produced by this method may be increased by applying a force across the plane of the backsheet layer (i.e. stretching the layer).

Suitable apertured formed films include films which have discrete apertures which extend beyond the horizontal plane of the garment facing surface of the layer towards the core thereby forming protuberances. The protuberances have an orifice located at its terminating end. Preferably said protuberances are of a funnel shape, similar to those described in U.S. Pat. No. 3,929,135. The apertures located within the plane and the orifices located at the terminating end of protuberance themselves maybe circular or non circular provided the cross sectional dimension or area of the orifice at the termination of the protuberance is smaller than the cross sectional dimension or area of the aperture located within the garment facing surface of the layer. Preferably said apertured performed films are uni directional such that they have at least substantially, if not complete one directional fluid transport towards the core.

Suitable macroscopically expanded films for use herein include films as described in for example in U.S. Pat. No. 4,637,819 and U.S. Pat. No. 4,591,523.

Suitable monolithic films include Hytrel™, available from DuPont Corporation, USA, and other such materials as described in Index 93 Congress, Session 7A "Adding value to Nonwovens", J-C. Cardinal and Y. Trouilhet, DuPont de Nemours international S.A, Switzerland such as Pebax™, available from Elf Atochem (France) and Estane™ available from B.F. Goodrich (Belgium).

Particularly preferred backsheets for the present invention comprise at least two layers comprising at least one layer selected from the above, such as microporous and apertured formed films and an additional layer which may also be selected from the above listed backsheets or may be a fibrous woven or nonwoven. The most preferred breathable backsheet component comprises a microporous film and an apertured formed film or a microporous and a hydrophobic woven or nonwoven material.

What is claimed is:

1. A process for joining the components of a disposable absorbent article, to one another, said article comprising at least a first component and a second component, said first component having a first surface and said second component having a second surface; said process comprising the steps of:

a) providing said first component in a machine direction, b) providing a slot coater;

c) providing a printing roll with an adhesive from said slot coater, wherein said printing roll has gravures, and wherein said gravures are filled with less than 90% of said adhesive;

d) contacting said first surface of said first component with said printing roll and transferring at least a portion of said adhesive from.said roll to said first surface;

e) providing said second component and contacting said first surface of said first component with said second surface of said second component, wherein said adhesive has an application temperature $T_a$ and said roll has a roll temperature $T_r$, wherein $T_a$ is greater than $T_r$.

2. A process according to claim 1, wherein said adhesive application temperature $T_a$ is at least 5° C. greater than the temperature of the printing roll $T_r$.

3. A process according to claim 1, wherein said adhesive application temperature $T_a$ is at least 10° C. greater than the temperature of the printing roll $T_r$.

4. A process according to claim 1, wherein said adhesive application temperature $T_a$ is at least 110° C.

5. A process according to claim 4, wherein said adhesive application temperature $T_a$ is at least 125° C.

6. A process according to claims 1, wherein said printing roll has a temperature $T_r$ of less than 130° C.

7. A process according to claim 6, wherein said printing roll has a temperature $T_r$ of less than 120° C.

8. A process according to claim 1, wherein said printing roll comprises a rotating transport roll for transporting said adhesive, said roll rotating such that it has a receiving portion of its rotation path and a delivery portion of its rotation path and wherein said roll receives said adhesive in said receiving portion of its rotation path, and said roll transports said adhesive from said receiving portion of its rotation path by rotation to said delivering portion of its rotation path where said roll delivers said adhesive to said first surface.

9. A process according to claim 8, wherein at least 75% of said adhesive present on said delivery portion of said rotation path of said rotating transport roll is delivered to said first surface.

10. A process according to claim 1, wherein said adhesive is a pressure sensitive adhesive.

* * * * *